US008807137B2

(12) United States Patent
Gillis et al.

(10) Patent No.: US 8,807,137 B2
(45) Date of Patent: *Aug. 19, 2014

(54) SELF-ANCHORING MAGNETIC FORCE IMPLANT DEVICES, SYSTEMS, AND METHODS

(75) Inventors: Edward M. Gillis, San Jose, CA (US); Craig Arthur Purdy, Sunnyvale, CA (US); Joe Paraschac, San Jose, CA (US); Scott Anthony McGill, San Ramon, CA (US); Ryan P. Boucher, San Francisco, CA (US); Lionel M. Nelson, Los Altos, CA (US)

(73) Assignee: Koninklijke Philips N.V., Eindhoven (NL)

( * ) Notice: Subject to any disclaimer, the term of this patent is extended or adjusted under 35 U.S.C. 154(b) by 887 days.

This patent is subject to a terminal disclaimer.

(21) Appl. No.: 11/645,918

(22) Filed: Dec. 27, 2006

(65) Prior Publication Data
US 2007/0209665 A1    Sep. 13, 2007

Related U.S. Application Data

(63) Continuation-in-part of application No. 11/603,753, filed on Nov. 22, 2006, now Pat. No. 8,001,971, and a continuation-in-part of application No. 11/397,744, filed on Apr. 4, 2006, now Pat. No. 7,721,740, which is a continuation-in-part of application No. 10/806,372, filed on Mar. 22, 2004, now Pat. No. 7,441,559, which is a continuation-in-part of application No. 10/718,254, filed on Nov. 20, 2003, now Pat. No. 7,360,542, and a continuation-in-part of application No. 10/656,861, filed on Sep. 6, 2003, now Pat. No. 7,188,627, and a continuation-in-part of application No. 10/236,455, filed on Sep. 6, 2002, now Pat. No. 7,216,648.

(60) Provisional application No. 60/754,839, filed on Dec. 29, 2005, provisional application No. 60/739,519, filed on Nov. 23, 2005, provisional application No. 60/441,639, filed on Jan. 22, 2003, provisional application No. 60/456,164, filed on Mar. 20, 2003.

(51) Int. Cl.
    *A61F 5/56* (2006.01)
(52) U.S. Cl.
    USPC ............................................ 128/848; 602/902
(58) Field of Classification Search
    USPC .................... 128/848, 859–862; 602/12, 902
    See application file for complete search history.

(56) References Cited

U.S. PATENT DOCUMENTS

| 4,304,227 A | 12/1981 | Samelson |
| 4,978,323 A * | 12/1990 | Freedman .................... 600/12 |

(Continued)

FOREIGN PATENT DOCUMENTS

DE    4307262    3/1993

*Primary Examiner* — Michael A. Brown

(57) ABSTRACT

A magnetic force system uses a magnetic implant sized and configured to be inserted in the pharynx and another magnetic implant sized and configured to be inserted in the tongue, palate, or pharynx. The system establishes different regions of magnetic interaction between the two implants across the airway, attracting and repelling, such that attractive interaction in one region of the implants combines with repelling interaction in another region of the implants, to provide a "hinge" structure. Alternatively, a magnetic force system that uses three magnetic implants sized and configured to be inserted in the tongue, pharynx, and palate, respectively. The tongue implant is attracted to the palatal implant, and repels the pharyngeal implant, forming a modified "hinge" structure. Forces of magnetic attracting bring tissue together to form a magnetic hinge joint, providing an anchor to stabilize the regions where repelling forces work to separate tissue to keep the airway open.

8 Claims, 10 Drawing Sheets

(56) References Cited

U.S. PATENT DOCUMENTS

| | | |
|---|---|---|
| 5,019,372 A | 5/1991 | Folkman et al. |
| 5,176,618 A * | 1/1993 | Freedman ............... 600/12 |
| 5,220,918 A | 6/1993 | Heide et al. |
| 5,373,859 A | 12/1994 | Forney |
| 5,465,734 A | 11/1995 | Alvarez et al. |
| 5,649,540 A | 7/1997 | Alvarez et al. |
| 5,792,067 A | 8/1998 | Karell |
| RE36,120 E | 3/1999 | Karell |
| 5,979,456 A | 11/1999 | Magovern |
| 5,988,171 A | 11/1999 | Sohn et al. |
| 6,231,496 B1 | 5/2001 | Wilk et al. |
| 6,244,865 B1 | 6/2001 | Nelson et al. |
| 6,250,307 B1 | 6/2001 | Conrad et al. |
| 6,390,096 B1 | 5/2002 | Conrad et al. |
| 6,401,717 B1 | 6/2002 | Conrad et al. |
| 6,408,851 B1 * | 6/2002 | Karell ............... 128/848 |
| 6,415,796 B1 | 7/2002 | Conrad et al. |
| 6,450,169 B1 * | 9/2002 | Conrad et al. ............... 128/897 |
| 6,490,885 B1 | 12/2002 | Wilkinson |
| 6,523,541 B2 * | 2/2003 | Knudson et al. ............... 128/897 |
| 6,523,542 B2 | 2/2003 | Knudson et al. |
| 6,636,767 B1 | 10/2003 | Knudson et al. |
| 6,742,524 B2 | 6/2004 | Knudson et al. |
| 6,955,172 B2 | 10/2005 | Nelson et al. |
| 7,073,505 B2 | 7/2006 | Nelson et al. |
| 7,077,143 B2 | 7/2006 | Knudson et al. |
| 7,077,144 B2 | 7/2006 | Knudson et al. |
| 7,107,992 B2 * | 9/2006 | Brooks et al. ............... 128/848 |
| 7,188,627 B2 | 3/2007 | Nelson et al. |
| 7,322,993 B2 * | 1/2008 | Metzger et al. ............... 606/151 |
| 2001/0047805 A1 | 12/2001 | Scarberry et al. |
| 2002/0066702 A1 | 6/2002 | Liu |
| 2004/0112390 A1 * | 6/2004 | Brooks et al. ............... 128/863 |
| 2005/0092332 A1 | 5/2005 | Conrad et al. |
| 2006/0241746 A1 * | 10/2006 | Shaoulian et al. ............... 623/2.37 |

\* cited by examiner

SELF-ANCHORING MAGNETIC FORCE IMPLANT DEVICES, SYSTEMS, AND METHODS

RELATED APPLICATIONS

This application claims the benefit of U.S. Provisional Patent Application Ser. No. 60/754,839, filed Dec. 29, 2005, and entitled "Self-Anchoring Magnetic Force Implant, Devices, Systems, and Methods." This application is also a continuation-in-part of co-pending U.S. patent application Ser. No. 11/603,753, filed Nov. 22, 2006, and entitled "Devices, Systems, and Methods for Stabilization or Fixation of Magnetic Force Devices Used in or On a Body," which claims the benefit of U.S. Provisional Patent Application Ser. No. 60/739,519, filed Nov. 23, 2005, and which is also continuation-in-part of co-pending U.S. patent application Ser. No. 11/397,744, filed Apr. 4, 2006 entitled "Devices, Systems, and Methods Using Magnetic Force Systems In or On Tissue," which is a continuation-in-part of co-pending U.S. patent application Ser. No. 10/806,372, filed Mar. 22, 2004 entitled "Devices, Systems, and Methods to Fixate Tissue Within the Regions of the Body, Such as the Pharyngeal Conduit," which is a continuation-in-part of U.S. patent application Ser No. 10/718,254, filed Nov. 20, 2003, now U.S. Pat. No. 7,360,542, entitled "Devices, Systems, and Methods to Fixate Tissue Within the Regions of the Body, Such as the Pharyngeal Conduit," which is a continuation-in-part of U.S. patent application Ser. No. 10/656,861, filed Sep. 6, 2003, now U.S. Pat. No. 7,188,627, entitled "Magnetic Force Devices, Systems, and Methods for Resisting Tissue Collapse within the Pharyngeal Conduit," which further claims the benefit of U.S. Provisional Patent Application Ser. No. 60/441,639, filed Jan. 22, 2003 and U.S. Provisional Patent Application Ser. No. 60/456,164, filed Mar. 20, 2003, and which is a continuation-in-part of U.S. patent application Ser. No. 10,236,455, filed Sep. 6, 2002, now U.S. Pat. No. 7,216,648, and entitled "System and Method for Moving and/or Restraining Tissue in the Upper Respiratory System." All of the foregoing are incorporated herein by reference.

FIELD OF THE INVENTION

The invention is directed to devices, systems, and methods for resisting tissue collapse in an airway e.g., for the treatment of sleep-related breathing disorders such as snoring, upper airway resistance syndrome and obstructive sleep apnea.

BACKGROUND OF THE INVENTION

I. Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans.

There are two types of sleep apnea: central and obstructive. Central sleep apnea, which is relatively rare, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. Normally, the muscles of the upper part of the throat keep the airway open to permit air flow into the lungs. When the muscles of the soft palate at the base of the tongue and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" may be as high as 20 to 30 or more per hour. These breathing pauses are almost always accompanied by snoring between apnea episodes, although not everyone who snores has the condition. Sleep apnea can also be characterized by choking sensations.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all persons and mammals, the frequency of blockages will determine the seriousness of the disease and opportunity for health damage. When the incidence of blockage is frequent, corrective action should be taken.

II. Sleep and the Anatomy of the Upper Airway

The upper airway consists of a conduit that begins at the nasal valve, situated in the tip of the nose, and extends to the larynx. Although all tissue along this conduit is dynamic and responsive to the respiratory cycle, only the pharynx (the portion that starts behind the nasal cavity and ends in its connections to the supraglottic larynx is totally collapsible.

The cross sectional area of the upper airway varies with the phases of the respiratory cycle. At the initiation of inspiration (phase I), the airway begins to dilate and then to remain relatively constant through the remainder of inspiration (Phase II). At the onset of expiration (Phase III) the airway begins to enlarge, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration. [ref: Schwab R J, Goldberg A N. Upper airway assessment: radiographic and other imaging techniques. Otolaryngol Clin North Am 1998;31:931-968]

Sleep is characterized by a reduction in upper airway dilator muscle activity. For the individual with obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx [ref: Isono S, Remmers J, Tanaka A Sho Y, Sato J, Nishino T. Anatomy of pharynx in patients with obstructive sleep apnea and in normal subjects. J Appl Physiol 1997:82:1319-1326.] Although this phenomenon is often accentuated at specific sites, such as the velopharyngeal level [Isono], studies of closing pressures [Isono] supports dynamic fast MRI imaging that shows narrowing and collapse usually occurs along the entire length of the pharynx. [ref: Shellock F G, Schatz C J, Julien P, Silverman J M, Steinberg F, Foo T K F, Hopp M L, Westbrook P R. Occlusion and narrowing of the pharyngeal airway in obstructive sleep apnea: evaluation by ultrafast spoiled GRASS MR imaging. Am J of Roentgenology 1992:158:1019-1024.].

III. Treatment Options

To date, the only modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months.

An alternative method would "splint" the airway during sleep that would give the benefits afforded by CPAP without some of its shortcomings would therefore be advantageous. In this method magnetic energy is used either attractively (opposite poles of two or more magnets facing one another, resulting in attractive forces) or repulsively (like poles of two or more magnets facing one another, resulting in forces which repel one another). Magnets implanted in the tongue interact either by attractive or repulsive forces with other magnets implanted in various organs of the upper airway system or external to the body within a neck collar.

Since the "splint" method using repelling magnetic forces did not eliminate all other destabilizing magnetic interaction, such as decentering forces, torques, etc., implants within the tongue and pharyngeal wall often were often difficult to stabilize in their specified locations. The destabilizing magnetic forces could cause the implants to fold or lose their shape. The implants could also decenter, rotate or otherwise migrate from their original implant position to a position of weaker/less effective magnetic repulsion or magnetic attraction that closes the airway.

The need remains for simple, cost-effective devices, systems, and methods for improved stabilization of magnetic force devices used in and/or on a body, including improved stabilization during placement and at an implanted position.

SUMMARY OF THE TECHNICAL FEATURES

The invention provides devices, and methods to keep the oropharynx open during sleep.

One aspect of the invention provides a magnetic force system comprising a magnetic implants sized and configured to be inserted in the airway, e.g., one in the oropharynx and another in the tongue. The system establishes different regions of magnetic interaction between the two implants across the airway, attracting and repelling. The attractive interaction in one region of the implants combines with repelling interaction in another region of the implants, to provide a "hinge" structure. Forces of magnetic attraction bring opposing implants and tissue together to form a magnetic hinge joint, stabilizing the regions where repelling forces work to separate tissue to keep the airway open.

A magnetic force system having regions of different magnetic interaction, attracting and repelling, can be variously configured. The size and configuration of the different regions can be altered to provide a larger repelling region than an attracting region, or vice versa. The size and configuration of the different regions can also be altered to provide greater stability in the repelling region. The magnetic hinge also holds the repelling sections of the implant in an orientation that allows them to strongly repel one another, thus not allowing the repelling implant sections to move to a position of weaker or less effective repulsion or to a position of magnetic attraction.

The invention is particularly useful to prevent sleep disordered diseases such as Obstructive Sleep Apnea (OSA) and hypopnea (a partial obstruction of the airway during sleep).

Other technical features shall be apparent based upon the accompanying description, drawings, and claims.

DESCRIPTION OF THE PREFERRED EMBODIMENTS

This Specification discloses various magnetic-based devices, systems, and methods for resisting collapse of fluid passageway in the body. The devices, systems, and methods are particularly well suited for resisting collapse of an airway, e.g., for treating sleep disordered breathing, including sleep apnea. For this reason, the devices, systems, and methods will be described in this context. Still, it should be appreciated that the disclosed devices, systems, and methods are applicable for use in treating other dysfunctions elsewhere in the body, which are not necessarily sleep disorder related.

Figure 1:
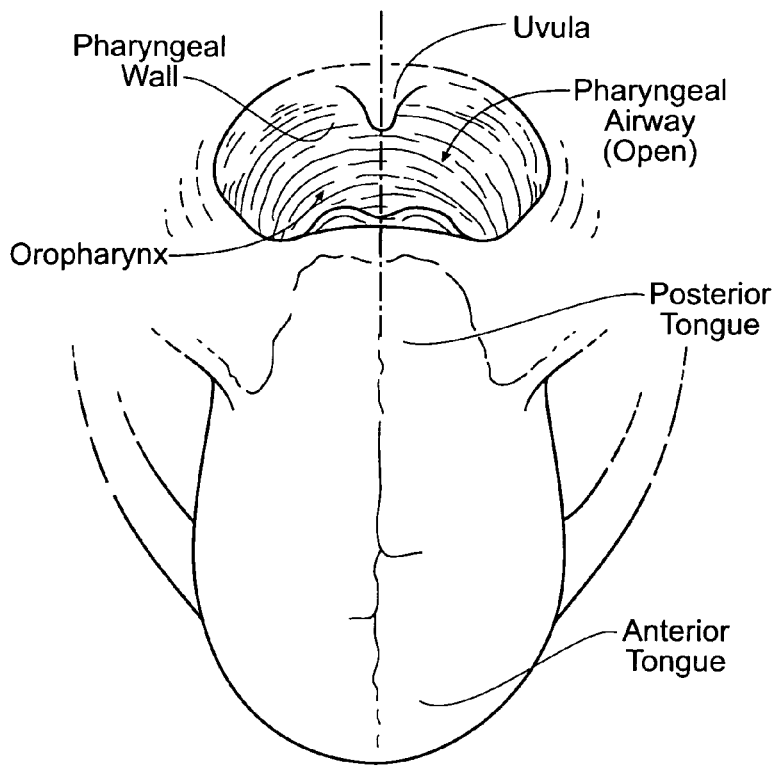
FIG. 1 is a caudal-facing horizontal plane view of the oropharynx, showing the tongue, pharyngeal wall, and the pharyngeal airway, in a normal open condition.

FIG. 1 shows, in an anatomic view, a caudal-facing horizontal plane view of the oropharynx, showing the general orientation of the tongue, pharyngeal wall, pharyngeal airway, and uvula (soft palate). Normally, the muscles of the upper part of the throat keep the airway open to permit air flow into the lungs, as FIG. 1 shows.

Figure 2:
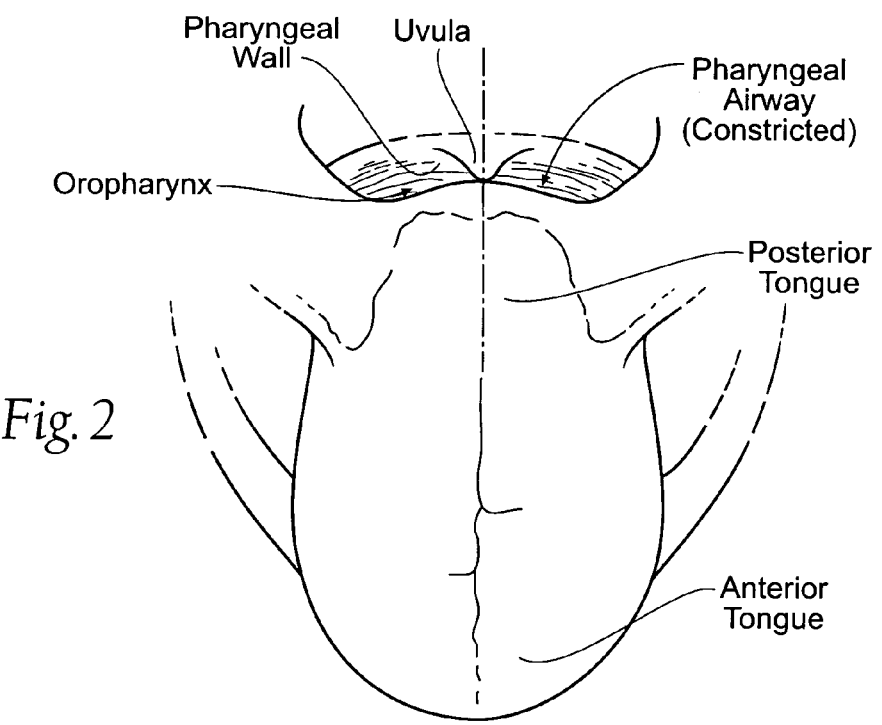
FIG. 2 is an anatomic view of the same region shown in FIG. 1 during an apneic episode, during which the tongue has relaxed during sleep and has fallen back against the posterior wall of the pharynx.

FIG. 2 shows, in an anatomic view, the same region of the oropharynx during an apneic episode, e.g., during sleep. The tongue has relaxed and has fallen back against a posterior pharyngeal wall. The airway is blocked or constricted, making breathing labored and noisy, or even stopping it altogether.

Figure 3:
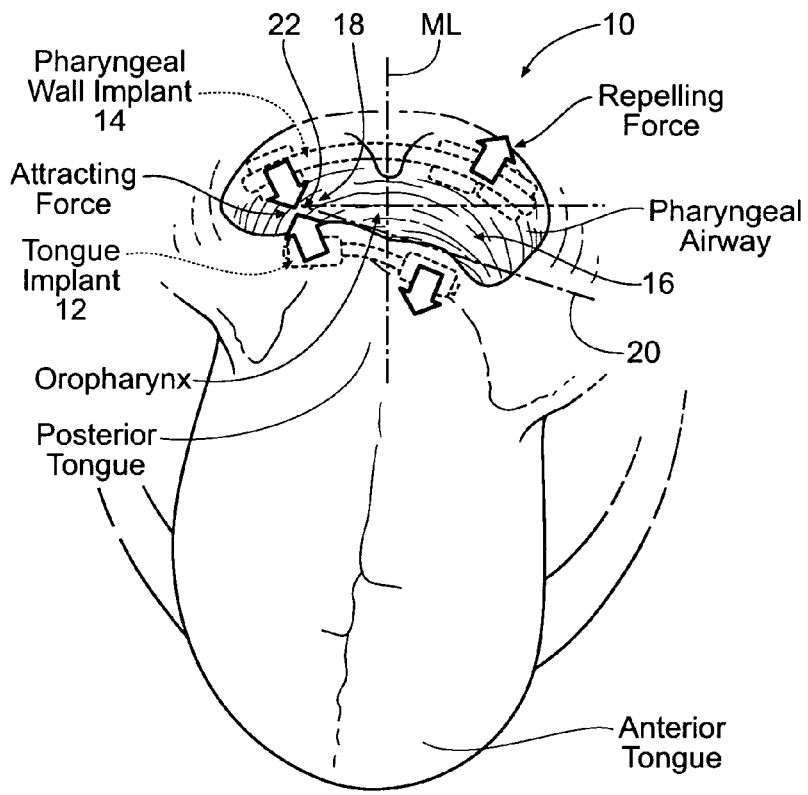
FIG. 3 shows in a caudal horizontal plane view a magnetic force system installed in the region shown in FIGS. 1 and 2 operating to keep the airway open.

FIG. 3 shows a magnetic force system 10 installed in the oropharynx. The system 10 serves to keep the airway open, thereby moderating or preventing an apneic episode.

The system 10 includes two separate magnetic implants 12 and 14, which are surgically inserted in the upper airway. The magnetic force system 10 resists total collapse of tissue in the airway between the pharyngeal wall and the posterior region of the tongue.

As generally shown in FIG. 3, the magnetic force system 10 includes a first magnetic component 12 implanted in the back of the tongue (desirably, posterior to the vallate papillae). The magnetic force system 10 also includes a second magnetic component 14 implanted in a posterior region of the oropharynx, i.e., in a posterior or posterior-lateral pharyngeal wall. As FIG. 3 shows, both components 12 and 14 span the midline ML of the airway, which is defined between these two tissue regions.

The magnetic polarities of the first and second magnetic components 12 and 14 on opposite sides of the midline ML are configured differently. The different configurations form two different magnetically interacting regions 16 and 18.

In the first region 16, the first and second magnetic components 12 and 14 magnetically interact by the generation of a repelling force between them. The magnetic repelling force keeps the portion of the posterior tongue in which the first region 16 is implanted from moving in a posterior direction toward the posterior pharyngeal wall. The magnetic repelling force keeps open the airway on one side of the midline ML.

In the second region 18, the first and second magnetic components 12 and 14 magnetically interact in an opposite fashion, by the generation of an attracting force between them. The attracting force draws the posterior portion of tongue in which the second region 18 is implanted toward the second magnetic component 14 implanted in a posterior region of the oropharynx. The magnetic attracting force narrows or closes the airway on the opposite side of the midline ML.

Figure 4:
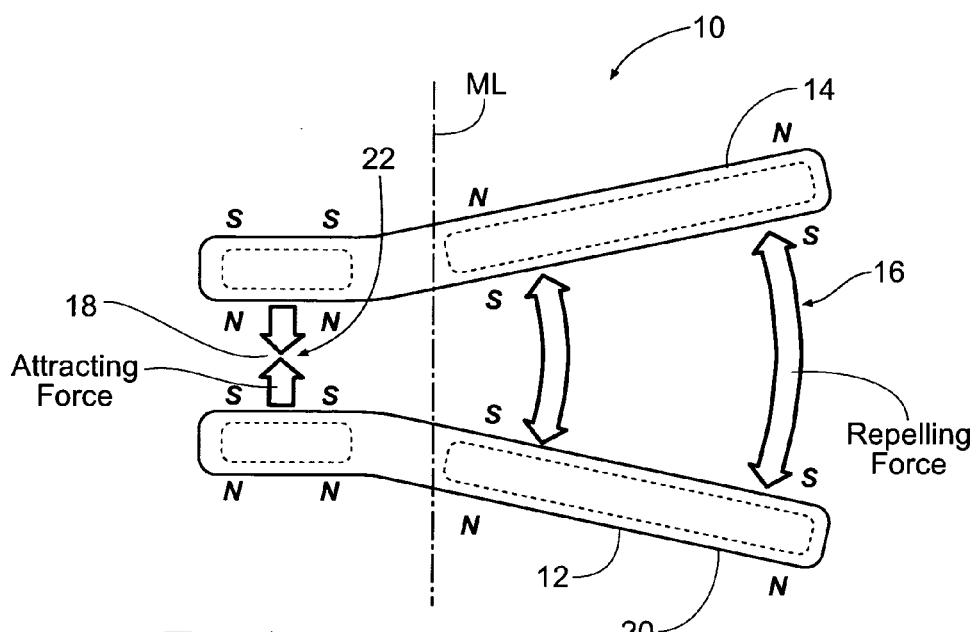
FIG. 4 is a diagrammatic view of the hinge joint that the system shown in FIG. 3 creates.

The juxtaposition of a magnetically attracting region 18 with a magnetically repelling region 16 forms a magnetic hinge 20 between the posterior of the tongue and a posterior region of the oropharynx (see FIG. 4). The magnetically attracting region 18 draws a portion of the two tissue regions together across the airway on one side of the midline ML, creating a magnetically stable hinge joint 22. The magnetically repelling region 16 separates an adjacent portion of the two tissue regions across the airway on the opposite side of the midline ML, which swing apart relative to the hinge joint 22, opening the airway.

As FIG. 3 best shows, due to the presence of the magnetic hinge, if the tongue relaxes and falls back against the posterior wall of the pharynx, the magnetically attracting regions 18 draw tissue together, stabilizing the tongue on one side of the midline ML and forming the hinge joint. The magnetically stable hinge joint allows the magnetically repelling regions 16 to work on the opposite side of the ML in an opposite manner, forcing tissue apart. The tongue is thereby stabilized at the hinge joint to the posterior wall of the oropharynx on one side of the midline. The magnets on the other side of the midline repel each other, moving the tissue away from contact and opening the airway.

It should be appreciated that the magnetic force system 10 generally shown in FIGS. 3 and 4 can be variously configured and arranged. As FIG. 4 shows, when two or more magnets are placed near each other, a repelling or attracting force will be present and will act upon the two or more magnets. A repelling force is generated when the poles of the same polarity [North (N) or South (S)] of two magnets are oriented toward each other (N-N or S-S). An attracting force is generated when the poles of the opposite polarity of two magnets are oriented toward each other (N-S or S-N). An attracting force can also be generated between a ferrous alloy and a magnet, regardless of the polarity.

A magnetic force can create difficulty in implanting or positioning magnets in a targeted tissue region, and can also contribute to the unwanted movement (i.e., migration or extrusion) of the magnets in the tissue region after implantation or positioning. A repelling magnetic force system is inherently less stable than a counterpart attracting magnetic system. It is desirable to provide magnetic field systems that are stabilized, both during implantation or positioning and after implantation during use.

Figure 5A:
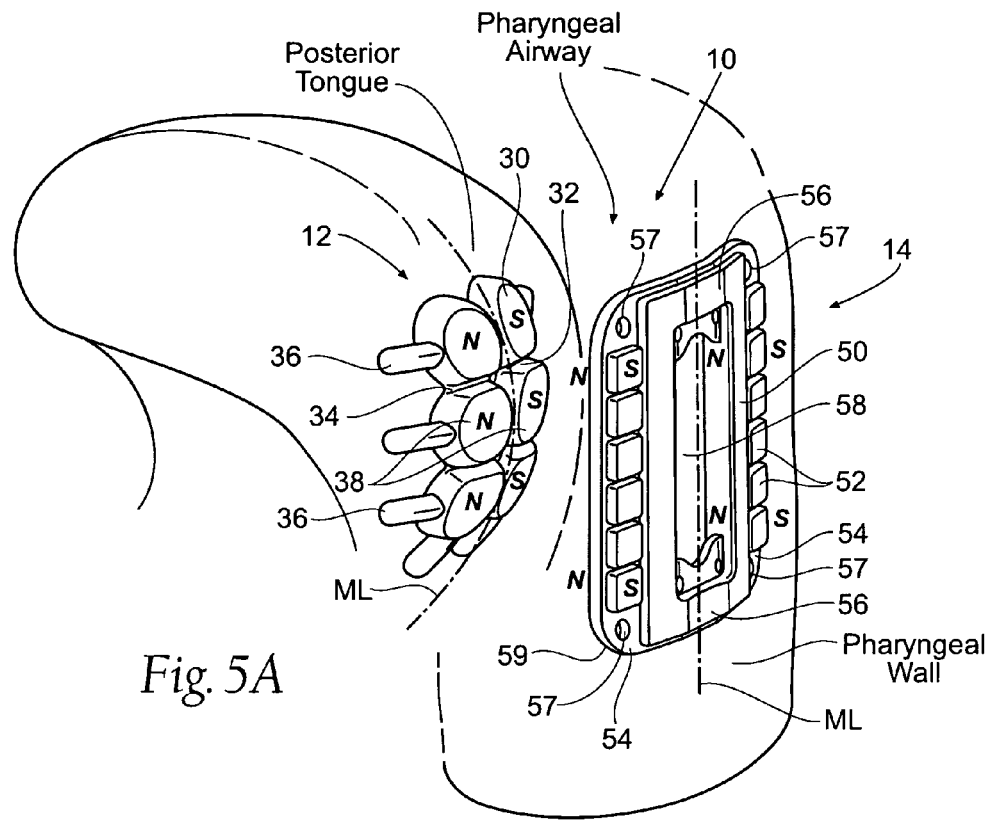
FIG. 5A is a perspective anatomic view of an embodiment of a system of a type shown in FIG. 3, which includes two separate magnetic implants, which, in use, are surgically inserted in the upper airway, one in the tongue and the other in a posterior pharyngeal wall.

FIG. 5A shows one illustrative embodiment of the magnetic force system 10. In this embodiment, the first magnetic component 12 comprises an implant 30 sized and configured for implantation in a tongue. The implant 30 comprises a flexible or compliant array of magnets 38 arranged in a polymer matrix. The implant matrix desirably provides preferential flexibility that takes into account the shape and movement of the tongue. The implant 30 includes flexible cross members 32 between the magnets 38 that extend along the long (longitudinal) axis that are thicker than (and thus less flexible than) the cross members 34 that extend between the magnets 38 along the short (transverse) axis. The design of the implant 30 promotes longitudinal stiffening and discourages the implant from folding in on itself. The thinner cross members 34 running across the narrower areas of the implant 30 allow for flexibility which closely mimics the movements of the tongue during normal oral activities. This embodiment of the invention has the advantage of combining implant stability with increased tolerance in the patient.

The implant 30 has other features to impart stability and comfort while implanted. For example, the implant 30 also includes integrated fixation tabs 36 that extend outward from the magnets 38 to engage adjacent tissue and provide enhanced fixation and stabilization. The implant also includes holes 40 for tissue in-growth or the placement of a tissue in-growth promoting material or bio-adhesive.

The cross members 34 that extend between the magnets 38 along the short (transverse) axis define the midline ML of the implant 30. The magnets 38 possess different polarities along the midline ML. As shown in FIG. 5A, along the left side of the midline ML, the polarities facing out of the tissue mass (i.e., toward the airway) are N poles. Along the right side of the midline ML, the polarities facing out of the tissue mass (i.e., toward the airway) are S poles.

In the arrangement shown in FIG. 5A, the second magnetic component 14 comprises an implant 50 sized and configured for implantation in a posterior pharyngeal wall. The implant 50 includes a flexible or compliant array of magnets 52 arranged in a polymer matrix. The matrix forms magnetic array sections 54 with spanning members 56 extending along the vertical (elongated) axis on both sides of the midline ML. The matrix is preformed with a concave bend, to conform to the pharyngeal wall. The center region 58 of the implant matrix is cut out to promote tissue in-growth to stabilize the implant 50.

The implant 50 has other features to impart stability and comfort while implanted, e.g., holes 57 for accommodating passage of sutures or fasteners for fixation, and rounded corner edges and beveled side edges 59 to promote faster healing.

In the embodiment shown in FIG. 5A, the polarity of the magnets 52 in the array are oriented in the same direction. As shown in FIG. 5A, along the both left and right sides of the array sections 54, the polarities facing outward of the tissue wall are N poles.

The outward facing poles of the implants 30 and 50, when implanted, create the first and second magnetic regions 16 and 18. On one side of the midline ML, the N poles of the tongue implant 30 face the N poles of the pharyngeal wall implant 50. The facing N-N poles magnetically repel each other, forming the first (repelling) magnetic region 16.

On the opposite side of the midline ML, the S poles of the tongue implant 30 face the N poles of the pharyngeal wall implant 50. The facing S-N poles magnetically attract each other, forming the second (attracting) magnetic region 18.

Figure 5B:
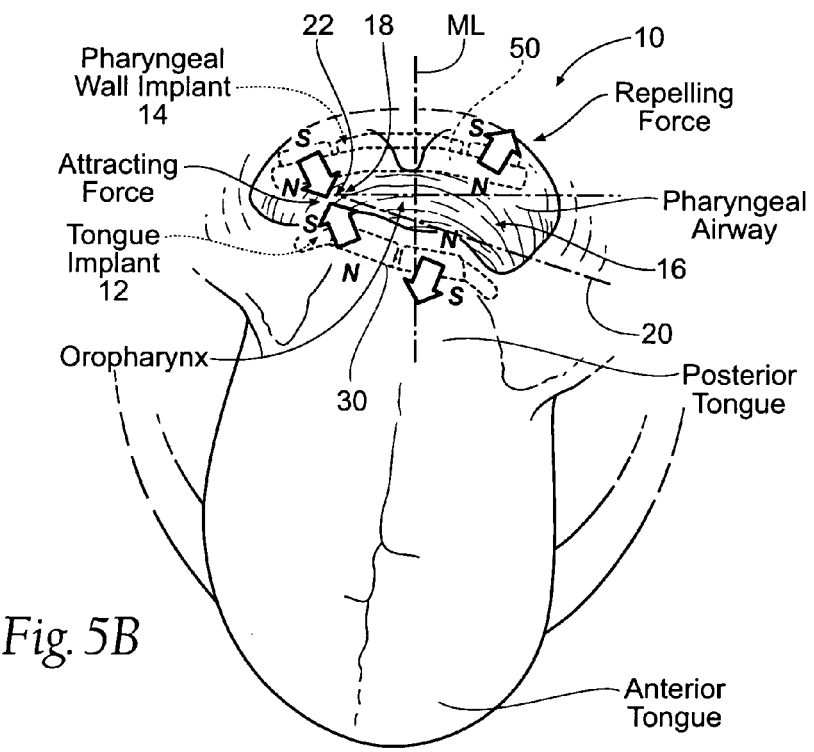
FIG. 5B is a diagrammatic view of the hinge joint that the system shown in FIG. 5A creates.

As FIG. 5B shows, the implants 30 and 50 shown in FIG. 5A, in use, magnetically interact to form the magnetic hinge 20. As the tongue relaxes and falls back against the posterior wall of the pharynx, the facing S-N poles of the magnetically attracting regions 18 draw tissue together, stabilizing the tongue on one side of the midline and forming the hinge joint 22. The magnetically stable hinge joint 22 allows the facing N-N poles of the magnetically repelling regions 16 to work on the opposite side of the ML in an opposite manner, forcing tissue apart. The tongue is thereby stabilized at the hinge joint 22 to the posterior wall of the oropharynx on one side of the midline. The magnets on the other side of the midline repel each other, moving the tissue away from contact and opening the airway.

Figure 6:
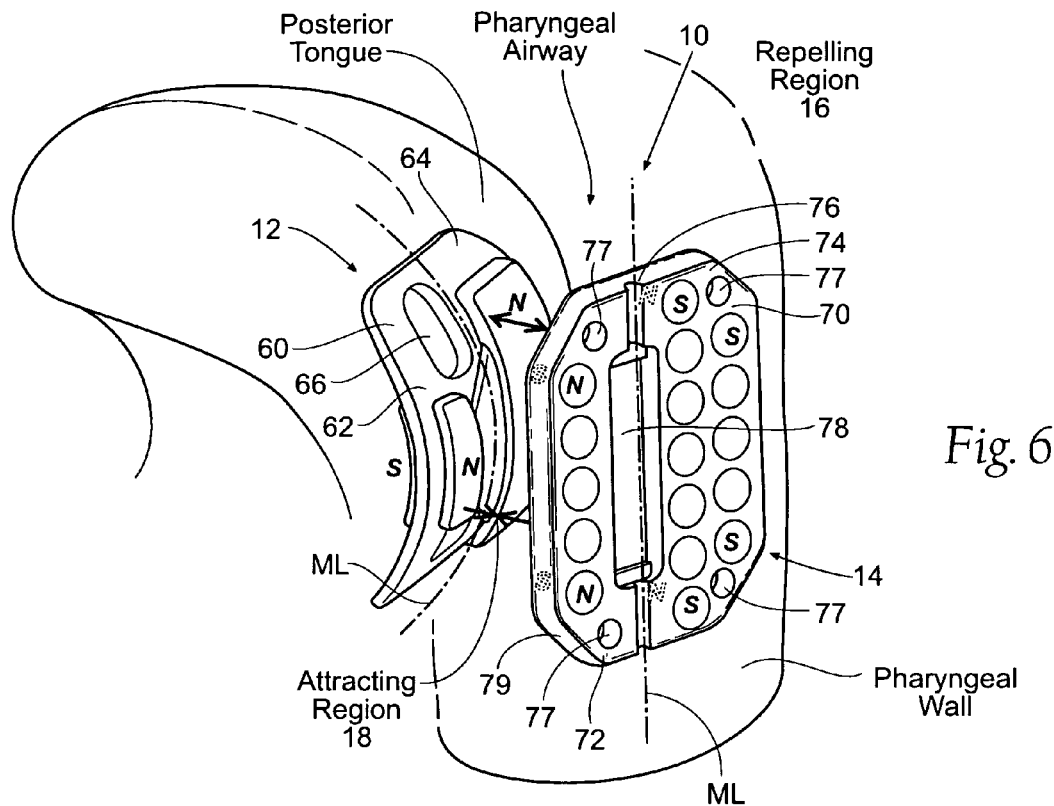
FIGS. 6, 7, and 8 are perspective anatomic views of alternative embodiments of a system of a type shown in FIG. 3.

FIG. 6 shows alternative embodiments of the first and second components 12 and 14. In this embodiment, the first magnetic component 12 comprises an implant 60 sized and configured for implantation in a tongue. The implant 60 comprises two magnetic regions 62 and 64 arranged in a flexible or compliant polymer matrix along a midline ML. The implant 60 is curved, to be well suited for implantation in the tongue. The implant's flowing curves permit a large area of the surrounding tissues to grow around and grip the implant 60 thus providing a natural anchor. The implant 60 includes holes or cutouts 66 that allow tissue in-growth, to further stabilize the implant and discourage implant migration.

In FIG. 6, the polarity of the magnetic regions 62 and 64 are oriented in the same way, with the N pole facing the airway. The magnetic region 64 presents a larger surface area than the magnetic region 62.

In FIG. 6, the second magnetic component 14 comprises an implant 70 sized and configured for implantation in a posterior pharyngeal wall. The implant 70 includes two magnetic array sections 72 and 74 arranged in a flexible or compliant polymer matrix. A spanning member 76 has a reduced thickness, compared to the thickness of the magnetic array sections 72 and 74. The thinner cross section of the spanning member 76 facilitates flexibility in the anterior-posterior direction, while the thicker magnetic array sections 72 and 74 discourage flexibility in the medial-lateral direction. This preferential flexibility allows the implant to remain in position because it closely mimics the movements of the surrounding anatomy.

The implant 70 has other features to impart stability and comfort while implanted, e.g., a cut-out section 78 for tissue in-growth, holes 77 for accommodating passage of sutures or fasteners for fixation, and rounded corner edges and beveled side edges 79 to promote faster healing.

In FIG. 6, the polarity of the magnetic array sections 72 and 74 are oriented in an opposite way along opposite sides of the spanning member 76. The magnetic array sections 72 and 74 also present different surface areas.

In the magnetic array section 72, the orientation of the pole facing the airway is S. In the magnetic array section 74, the orientation of the pole facing the airway is N. The magnetic array section 74 has a larger surface area than the surface area of the magnetic array section 72.

When implanted the implants 60 and 70 magnetically interact to form the magnetic hinge, as previously described. The N pole of the smaller surface area magnetic section 62 of the tongue implant 60 faces the S pole of the smaller surface area magnetic array section 72 of the pharyngeal wall implant 70, forming the magnetic attracting region 18. The N pole of the larger surface area magnetic section 64 of the tongue implant 60 faces the N pole of the larger surface area magnetic array section 72 of the pharyngeal wall implant 70, forming the magnetic repelling region 16.

As the tongue relaxes and falls back against the posterior wall of the pharynx, the facing S-N poles of the magnetically attracting regions 18 draw tissue together, stabilizing the tongue on one side of the midline ML and forming the hinge joint. The magnetically stable hinge joint allows the facing S-S poles of the magnetically repelling regions 16 to work on the opposite side of the ML in an opposite manner, forcing tissue apart. The tongue and implants are thereby stabilized at the hinge joint to the posterior wall of the oropharynx on one side of the midline. The magnets on the other side of the midline repel each other, moving the tissue away from contact and opening the airway.

In the embodiment shown in FIG. 6, the magnetic regions 16 and 18 possess different surface areas. In FIG. 6, the region of attraction, forming the hinge joint, has a smaller surface area than region of repelling. Thus, more tissue is repelled to open the airway than is attracted to stabilize the magnetic force system 10.

Furthermore, the magnetic section 62 is considerably shorter than the magnetic section 72. This difference in length avoids the potentially offset position of the magnetic section 62 as the magnetically attracting regions do not attract one another until the implants are more aligned. Also, the magnetic section 62 is rectangular in shape, providing some length of attracting region to avoid the implants rotating relative to one another around the hinge point.

Figure 7:
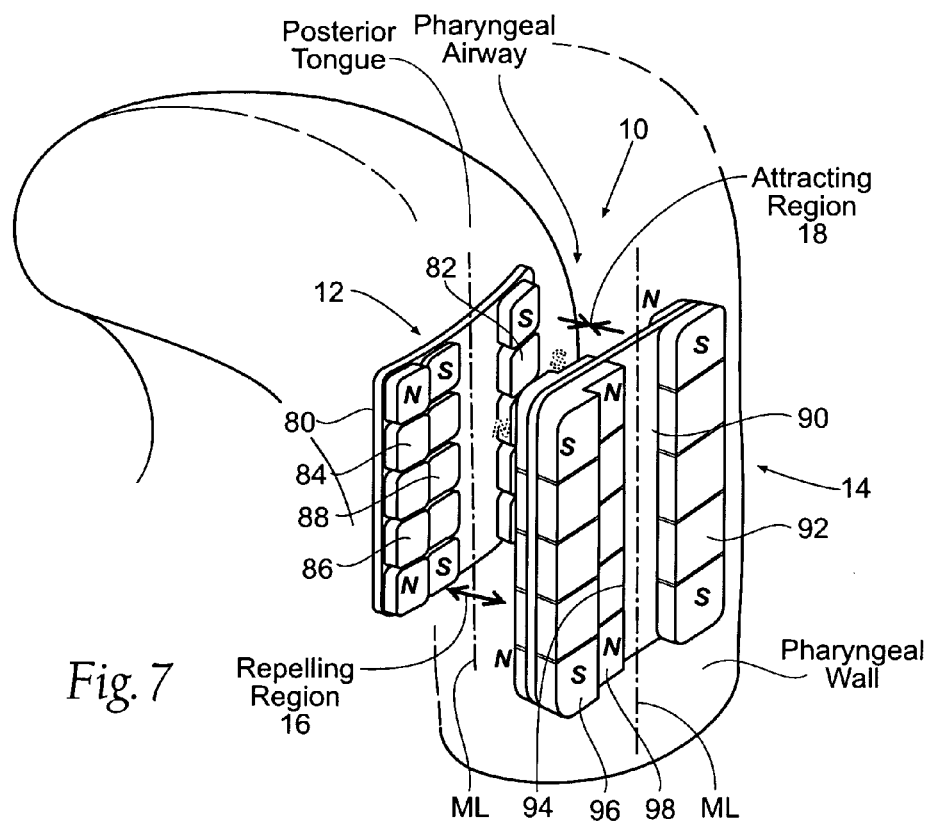

FIG. 7 shows alternatively orientations of magnetic forces forming the first and second regions 16 and 18. In FIG. 7, the first magnetic component 12 comprises an implant 80 sized and configured for implantation in a tongue. The tongue implant 80 comprises two magnetic regions 82 and 84 arranged in a flexible or compliant polymer matrix along a midline ML.

In FIG. 7, the second magnetic component 14 comprises an implant 90 sized and configured for implantation in a pharyngeal wall. The pharyngeal wall implant 90 comprises two magnetic regions 92 and 94 arranged in a flexible or compliant polymer matrix along a midline ML. When implanted, the magnetic regions 82 and 92 attract, forming the magnetic hinge joint, while the magnetic regions 84 and 94 repel.

Like the implants 60 and 70, the surface areas of the magnetic regions 82 and 84 on the tongue implant 80, as well as the interacting magnetic regions 92 and 94 on the pharyngeal wall implant 90 differ—the surface areas of the regions 84/94 that, in use, repel are larger than the surface areas of the region 82/92 that, in use, attract.

Also, in FIG. 7, the magnetic regions 84/94 include two longitudinal columns of magnets of opposite lateral polarity. For example, the magnetic region 84 of the tongue implant 80, comprises two longitudinal columns of 86 and 88 of magnets extending in along the midline ML. In one longitudinal column 88, the S poles are oriented to face the airway. In the other adjacent longitudinal column 86, the N poles are oriented to face the airway. The longitudinal columns 86 and 88 thus have along their lateral axis (transverse the midline ML) opposite polarities.

Likewise, the magnetic region 94 of the pharyngeal wall implant 90, comprises two longitudinal columns 96 and 98 of magnets of opposite lateral polarity. In one longitudinal column 96, the S poles are oriented to face the airway. In the other adjacent longitudinal column 98, the N poles are oriented to face the airway. The longitudinal columns 96 and 98 thus have along their lateral axis (transverse the midline ML) opposite polarities.

When implanted, the column 86 of N magnetic poles on the tongue implant 80 repels the interacting column 96 of N magnetic poles on the pharyngeal wall implant 90. Likewise, the column 88 of S magnetic poles on the tongue implant 80 repels the interacting columns 98 of S magnetic poles on the pharyngeal wall implant 90.

The juxtaposition of adjacent columns 86 and 88 on the tongue implant 80 having unlike polarity between them, which, in use, magnetically repel corresponding adjacent columns 96 and 98 on the pharyngeal wall implant 90, also having unlike polarity between them, provides a repelling system that is more stable than a repelling system between single columns of like polarity magnets or between adjacent columns of like polarity.

Figure 8:
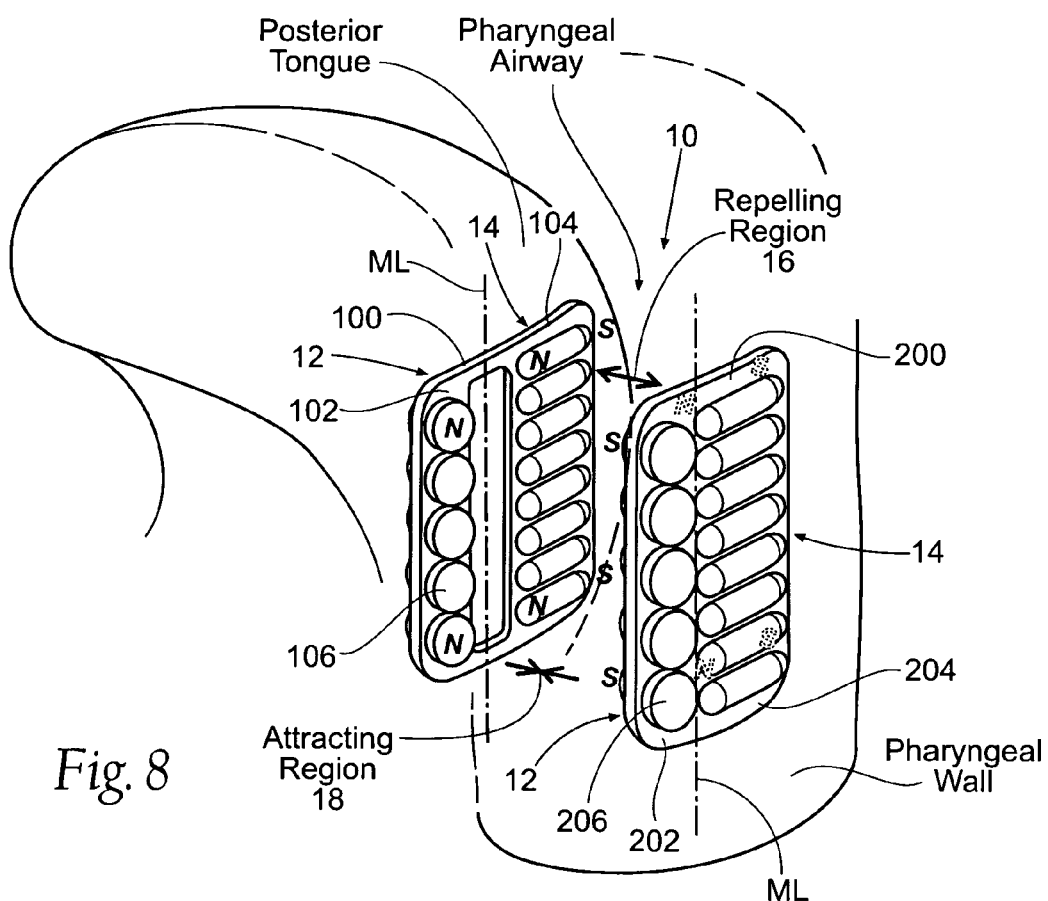

FIG. 8 shows yet another alternative orientation of magnetic forces forming the first and second regions 16 and 18. In FIG. 8, the first and second magnetic component 12 and 14 comprise, respectively, a suitable tongue implant 100 and a suitable pharyngeal wall implant 200. The tongue implant 100 comprises two magnetic regions 102 and 104 arranged in a flexible or compliant polymer matrix along a midline ML. Likewise, the pharyngeal wall implant 200 comprises two magnetic regions 202 and 204 arranged in a flexible or compliant polymer matrix along a midline ML. When implanted, the magnetic regions 102 and 202 attract, forming the magnetic hinge, while the magnetic regions 104 and 204 repel.

FIG. 8 shows alternative structural arrangements, in which the attracting magnetic regions 102 and 202 are sized and configured differently than the repelling magnetic regions 104 and 204, and in which the repelling magnetic regions 16 comprise longitudinally oriented magnets each having laterally opposed magnetic poles N-S.

In FIG. 8, the attracting magnetic regions 102 and 202 are configured as magnetic discs 106 and 206 having polarities that, in use, are oriented toward the airway in an attracting relationship N-S.

In FIG. 8, the repelling magnetic regions 104 and 204 are configured as bar magnets, each having opposite lateral poles N and S, which, in use, are oriented in a repelling relationship across the airway N-N and S-S. The orientation of the repelling magnet regions 104 and 204 shown in FIG. 8 thereby comprises a north magnetic polarity along one longitudinal column and a south magnetic polarity along the other longitudinal column, providing stability in the repelling region like that provided by the repelling magnetic regions 104 and 204 in FIG. 7.

FIGS. 9A to 9C and 10A to 10C show other alternative embodiments of a magnetic component 12, which, in use, is intended to be implanted in a tongue.

Figure 9A:
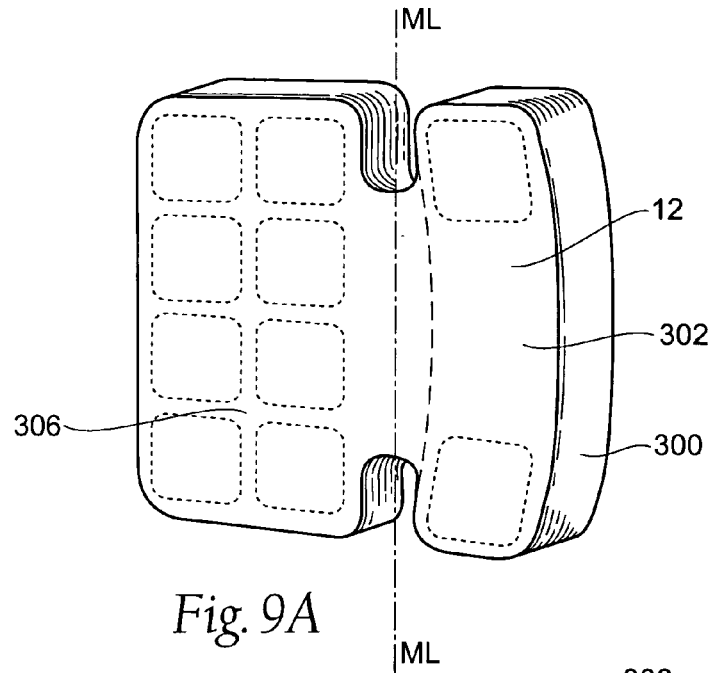
FIGS. 9A and 9B are, respectively, a perspective front view and an elevation view of a magnetic a tongue implant a portion of which has a flexible convex shape that flattens in the presence of an attracting magnetic force to align with a counterpart magnetic implant in a pharyngeal wall.

In FIG. 9A, the magnetic component 12 comprises an implant 300 sized and configured for implanting in a tongue. The tongue implant 300 comprises two magnetic regions 302 and 306 arranged in a flexible or compliant matrix along midline ML. As FIG. 9C shows, the tongue implant 300 is, in use, intended to magnetically interact with an implant 14 sized and configured for implanting in a pharyngeal wall. When implanted, the magnetic region 302 of the tongue implant 300 is attracted to a corresponding region on pharyngeal wall implant 14, forming a magnetic attracting region 18, while the magnetic region 306 of the tongue implant 300 is repelled by a corresponding region on the pharyngeal wall implant 14, forming a magnetic repelling region 16. A system 10 having magnetic hinge joint 20 as previously described is thereby created.

Figure 9B:
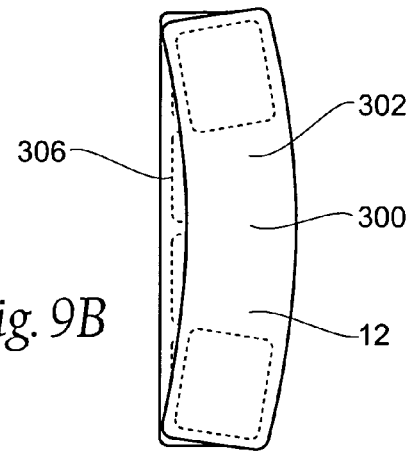
Figure 9C:
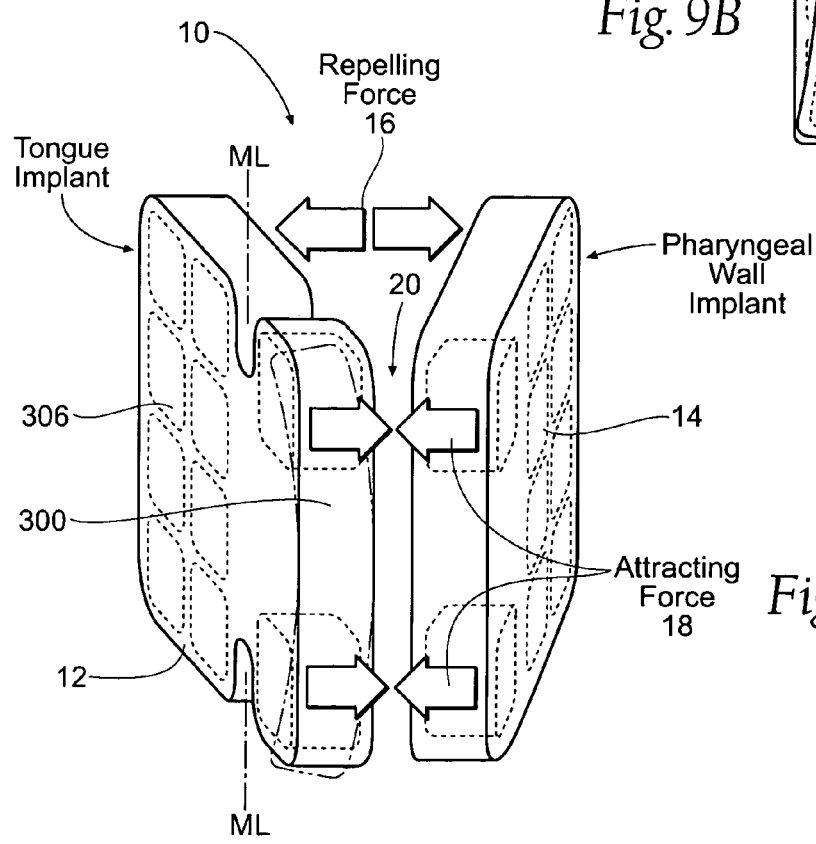
FIG. 9C is a perspective view of the magnetic tongue implant shown in FIGS. 9A and 9B interacting with a counterpart magnetic implant in a pharyngeal wall, showing the hinge joint that the interaction creates.

As shown in FIGS. 9A and 9B, the magnetic region 302 of the tongue implant 300 comprises a structure with resilient memory to cause it to normally flex and assume a convex shape, i.e., it is normally bowed outward toward the pharyngeal wall implant 14, as shown in phantom lines in FIG. 9C. As best shown in solid lines in FIG. 9C, once the normally flexed region 302 of the tongue implant 300 experiences the attracting magnetic field of the region 18, the convex region 302 resilient straightens out, allowing the tongue implant 300 to properly align itself with the pharyngeal wall implant 14.

Figure 10A:
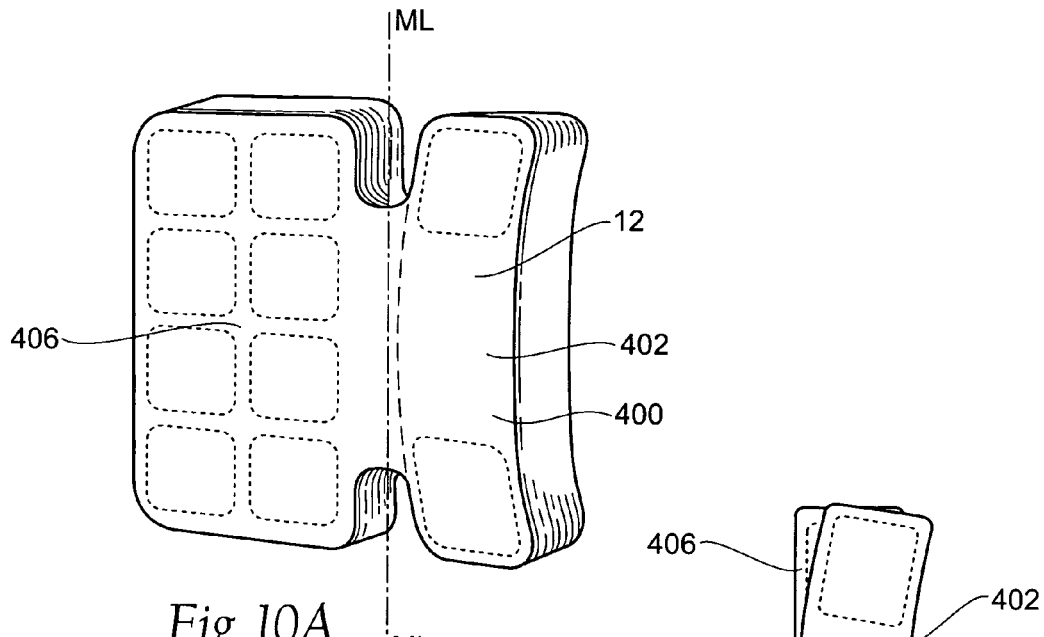
FIGS. 10A and 10B are, respectively, a perspective front view and an elevation view of a magnetic a tongue implant a portion of which has a flexible concave shape that flattens in the presence of an attracting magnetic force to align with a counterpart magnetic implant in a pharyngeal wall.
Figure 10B:
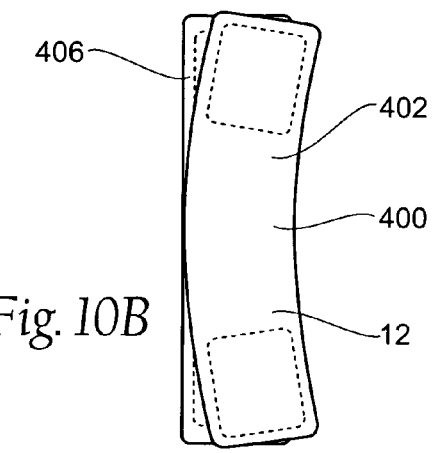
Figure 10C:
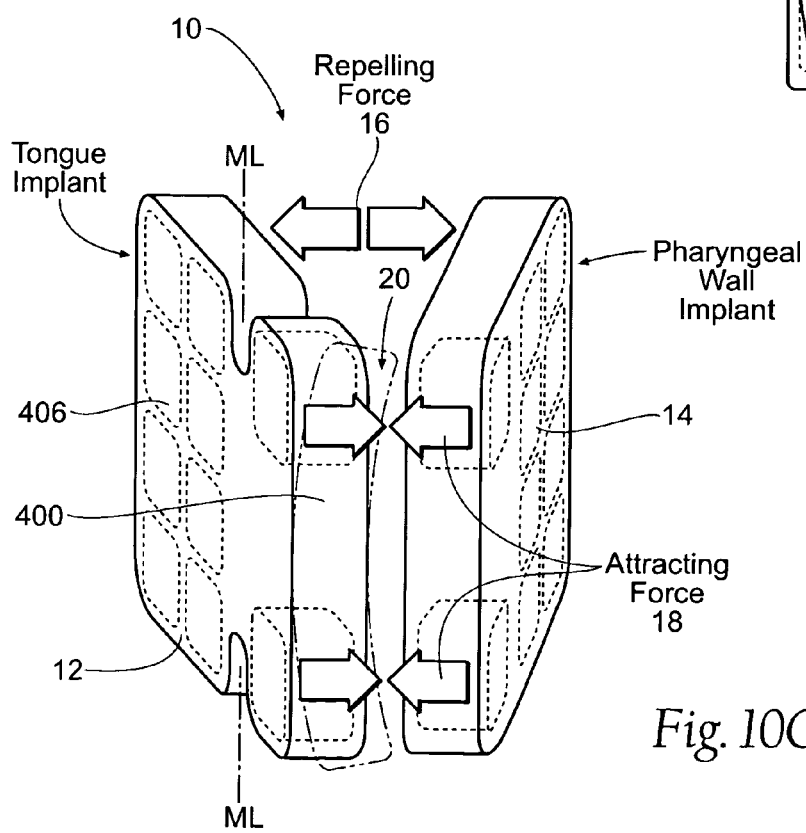
FIG. 10C is a perspective view of the magnetic tongue implant shown in FIGS. 10A and 10B interacting with a counterpart magnetic implant in a pharyngeal wall, showing the hinge joint that the interaction creates.

In FIGS. 10A, 10B, and 10C show a magnetic tongue implant 400 of the general type shown in FIGS. 9A, 9B, and 9C. The tongue implant 400 comprises two magnetic regions 402 and 406 arranged in a flexible or compliant matrix along midline ML. Magnetic region 402 is attracted to a corresponding region on a pharyngeal wall magnetic implant 14 (see FIG. 10C), while magnetic region 406 of the tongue implant 400 and its corresponding region on pharyngeal wall implant 14 repel, thereby forming a system 10 with the magnetic hinge joint 20.

As shown in FIGS. 10A and B, the magnetic region 402 of the tongue implant 400 comprises a structure with resilient memory to cause it to normally flex and assume a concave shape, i.e., it is normally bowed inward away from the pharyngeal wall implant 14, as also shown in phantom lines in FIG. 10C. As best shown in solid lines in FIG. 10C, once the normally flexed region 402 of the tongue implant 400 experiences the attracting magnetic field of the region 18, the concave region 402 resilient straightens out, allowing the tongue implant 400 to properly align itself with the pharyngeal wall implant 14.

Figure 11A:
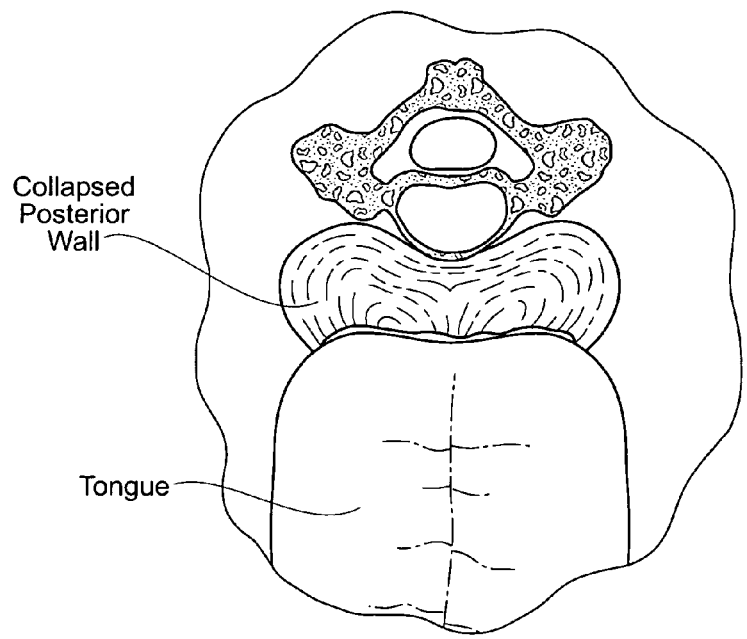
FIG. 11A is a caudal-facing horizontal plane view of the oropharynx, showing the tongue, pharyngeal wall, and the pharyngeal airway, in which a posterior pharyngeal wall has collapsed, obstructing the airway.
Figure 11B:
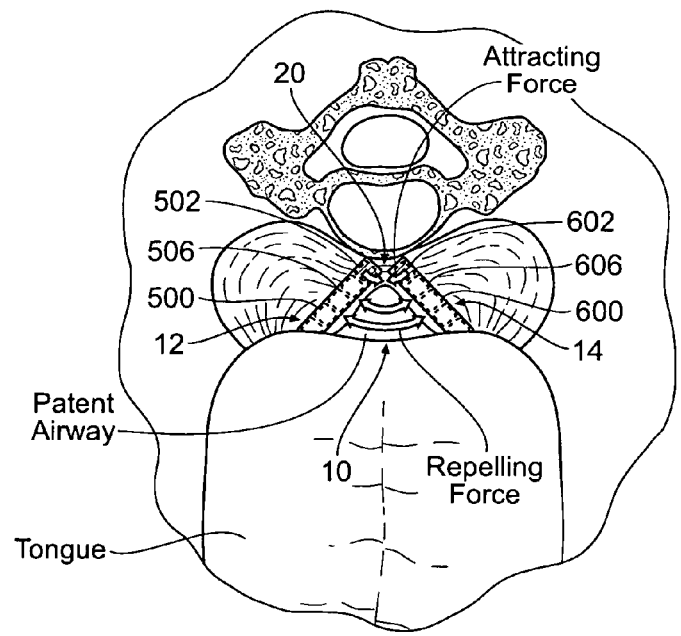
FIG. 11B is a caudal-facing horizontal plane view of the same region shown in FIG. 11A, showing a magnetic force system that has been installed in the pharyngeal wall to create a magnetic hinge joint that operates to keep the airway open.

FIG. 11B shows another alternative embodiment of a magnetic force field system 10 that includes a magnetic hinge joint 20. In FIG. 11B, the system 10 comprising two magnetic implants 500 and 600, each sized and configured to be implanted in a pharyngeal wall region. This region is shown prior to implantation in FIG. 11A, showing the tongue, pharyngeal wall, and the pharyngeal airway. As shown in FIG. 11A, a posterior pharyngeal wall has collapsed toward the tongue, obstructing the airway. In FIG. 11B, the implants 500 and 600 have been installed in the pharyngeal wall region, forming a magnetic force system 10 that creates a magnetic hinge joint 20 that operates to keep the airway open.

More particularly, pharyngeal implant 500 comprises two magnetic regions 502 and 506 arranged in a flexible compliant matrix in the manners previous shown. Pharyngeal implant 600 also comprises two magnetic regions 602 and 606. Magnetic region 502 on the implant 500 is attracted to its corresponding region 602 on the implant 600, while magnetic region 506 on the implant 500 and its corresponding magnetic region 606 on implant 600 repel, forming the magnetic hinge joint 20 as previously described. As FIG. 11B shows, the magnetic hinge joint 20 lifts the collapsed posterior wall and thereby maintains a patent airway.

Figure 12A:
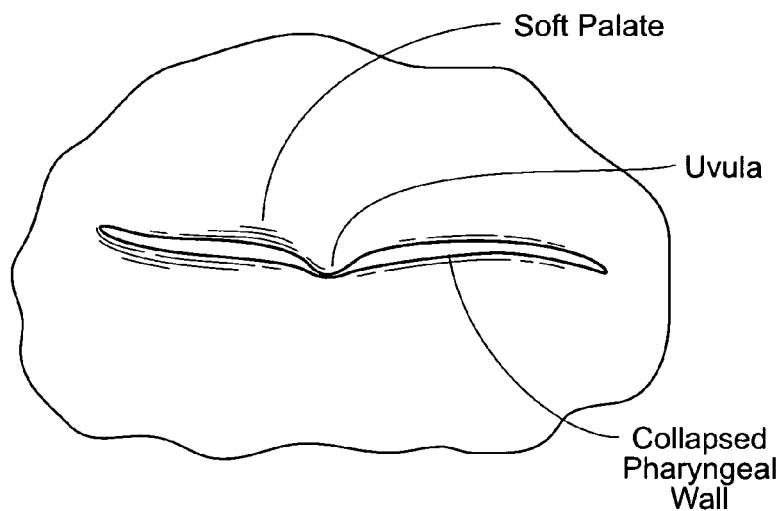
FIG. 12A is a caudal-facing horizontal plane view of the oropharynx, showing the soft palate, uvula, pharyngeal wall, and the pharyngeal airway, in which a posterior pharyngeal wall has collapsed, obstructing the airway.
Figure 12B:
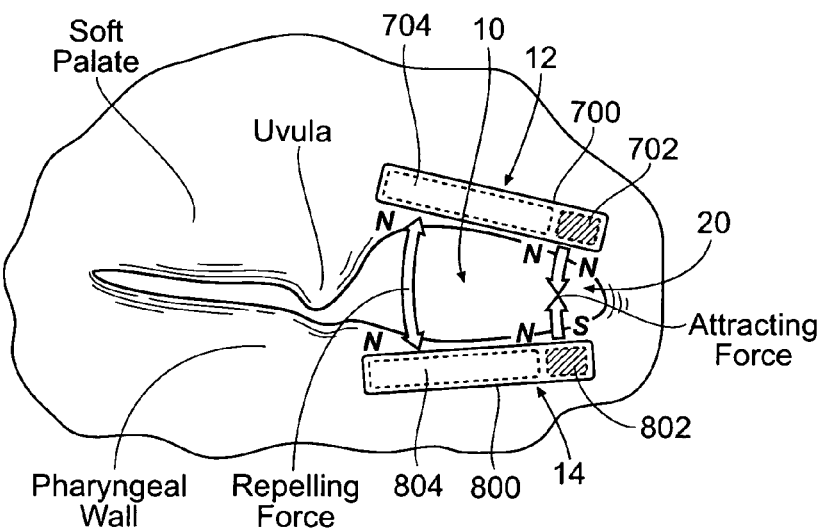
FIG. 12B is a caudal-facing horizontal plane view of the same region shown in FIG. 12A, showing a magnetic force system that has been installed in the palate and pharyngeal wall to create a magnetic hinge joint that operates to keep the airway open.

FIG. 12B shows another alternative embodiment of a magnetic force field system 10 that includes a magnetic hinge joint 20. In FIG. 12B, the system 10 comprising two components 12 and 14, respectively magnetic implants 700 and 800. Magnetic implant 700 is sized and configured for implanting in a region of the soft palate, e.g. near the uvula, as shown in FIG. 12B. Magnetic implant 800 is sized and configured for implanting a pharyngeal wall region, as FIG. 12B also shows. These regions are shown prior to implantation in FIG. 12A, showing the soft palate, uvula, pharyngeal wall, and the pharyngeal airway, in which a posterior pharyngeal wall has collapsed, obstructing the airway. In FIG. 12B, the magnetic force system 10 comprising the soft palate implant 700 and the pharyngeal wall implant 800 has been installed to create a magnetic hinge joint 20 that operates to keep the airway open.

More particularly, the palate implant 700 comprises two magnetic regions 702 and 706 arranged in a flexible compliant matrix in the manners previously described. The pharyngeal implant 800 likewise comprises two magnetic regions 802 and 806. The magnetic region 702 of the palate implant 700 is attracted to corresponding region 802 on the pharyngeal implant 800, while the magnetic region 706 on the palate implant 700 and the corresponding magnetic region 806 on the pharyngeal implant 700 repel, thereby forming the magnetic hinge joint 20. The magnetic hinge joint 20 lifts the collapsed posterior wall away from the soft palate, maintaining a patent airway.

Figure 13A:
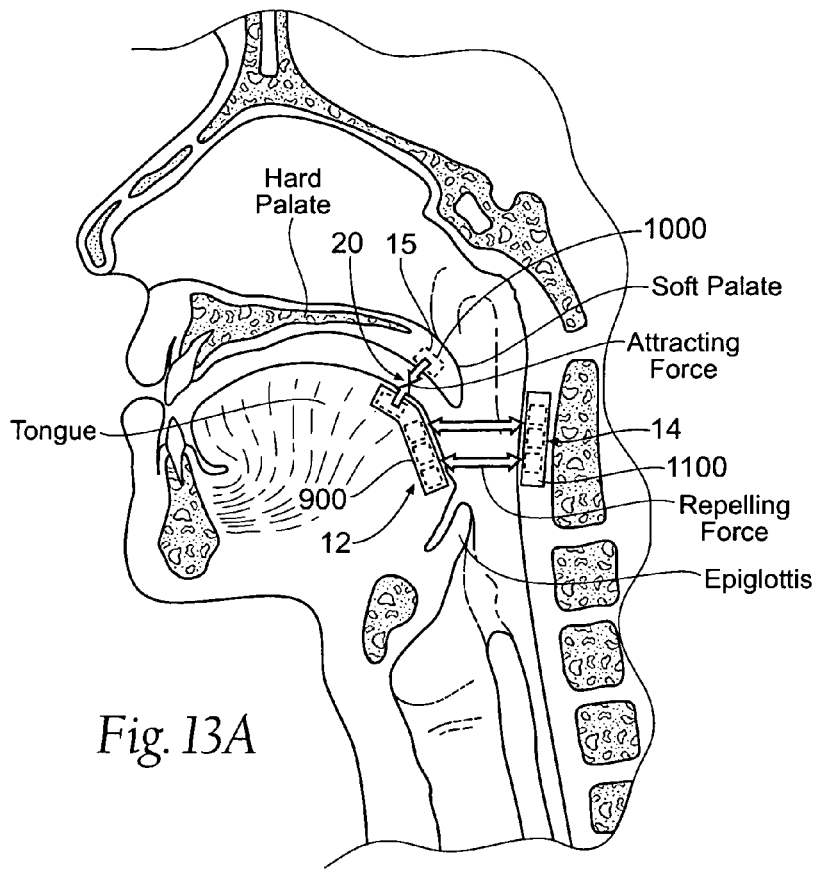
FIG. 13A is a lateral sectional view of the oropharynx, showing the soft palate, tongue, and pharyngeal wall, in which a magnetic force system has been installed in the soft palate, tongue, and pharyngeal wall that operates to keep the airway open, the magnetic force field system including a region of magnetic attracting interaction between the soft palate and a portion of the tongue that create a magnetic hinge joint that stabilizing a region of magnetic repelling interaction between the back of the tongue and the posterior pharyngeal wall.

FIG. 13A shows yet another alternative embodiment of a magnetic force field system 10 that includes a magnetic hinge joint 20. In FIG. 13A, the system 10 comprises three magnetic implant components 12, 14, and 15. Magnetic implant component 12 is sized and configured for implanting in a tongue. Magnetic implant component 14 is sized and configured for implanting in a pharyngeal wall. Magnetic implant component 15 is sized and configured for implanting in a soft palate. As FIG. 13A shows, the soft palate implant 15 is attracted to the tongue implant 12, while the pharyngeal implant 14 is magnetically repelled by the tongue implant 12.

Figure 13B:
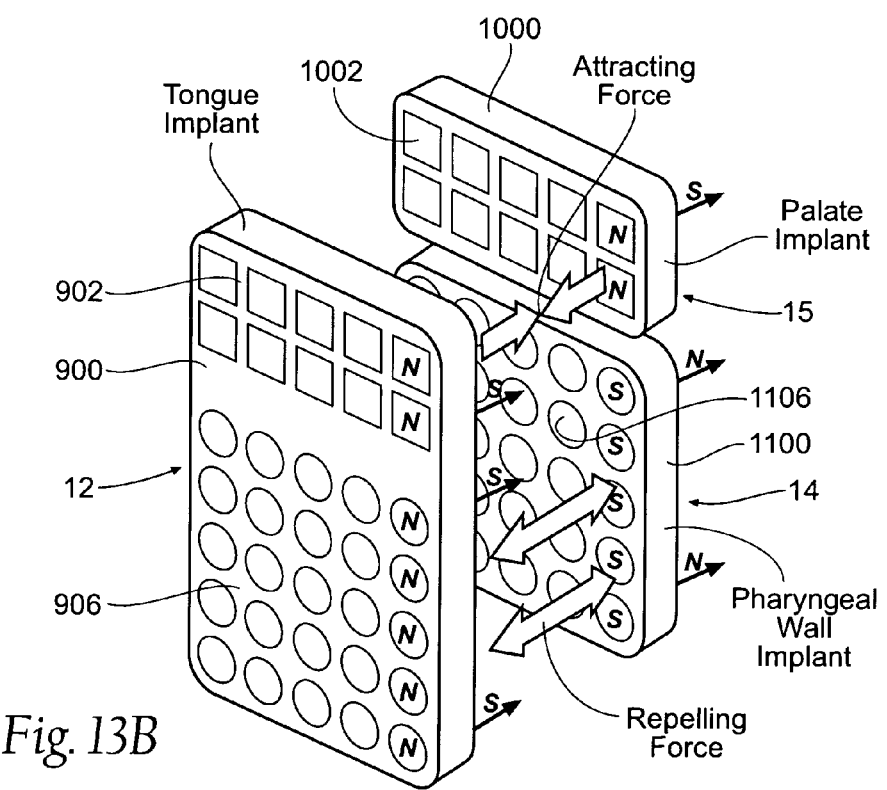
FIG. 13B is a perspective view of the magnetic implants in the palate, tongue, and pharyngeal wall that comprise the force field system shown in FIG. 13A.

The system 10 shown in FIG. 13A can be configured and arranged in various ways. In the embodiment shown in FIG. 13B, the magnetic component 12 comprises a magnetic tongue implant 900. The tongue implant 900 comprises two magnetic regions 902 and 906 arranged in a flexible compliant matrix in the manners previously described. The magnetic regions 902 and 906 have the same polarities (e.g., S facing the airway), but differ in surface area. The magnetic region 902 has a smaller surface area than magnetic region 906. In use, the smaller magnetic region 902 is intended to magnetically interact with a relatively small palatal component 15, while the larger magnetic region 906 is intended to magnetically interact with a relatively larger pharyngeal component 14.

The magnetic component 15 comprises a magnetic palatal implant 1000. The palatal implant 1000 comprises a magnetic region 1002. The magnetic region 1002 has the same polarity that is opposite to the polarity of the magnetic region 902 on the tongue implant 900, with which it is intended to magnetically interact by attraction. In the illustrated embodiment, the polarity of the magnetic region 1002 on the palatal implant 1000 is N facing the airway, which magnetically interacts in the desired way by attraction with the opposite polarity of the magnetic region 902 of the tongue implant 900 (S facing the airway).

The magnetic component 14 comprises magnetic pharyngeal implant 1100. Pharyngeal implant 1100 comprises a magnetic region 1106. The magnetic region 1106 has the same polarity that is same as the polarity of the magnetic region 906 on the tongue implant 900, with which it is intended to magnetically interact by repelling. In the illustrated embodiment, the polarity of the magnetic region 1106 on the pharyngeal implant 1100 is S facing the airway, which magnetically interacts in the desired way by repelling with the same polarity of the magnetic region 906 of the tongue implant 900 (S facing the airway).

The differences in polarity of the palatal implant 1000 and the pharyngeal implant 1100 relative to the tongue implant 900 forming a modified magnetic hinge joint 20 (see FIG. 13A), which stabilizes the position of the tongue implant 900 in its desired position. Magnetic regions 1106 and 906 interact by repelling each other and thus maintaining a patent airway. FIG. 13A shows the location of the tongue, palatal, and pharyngeal implants 900, 1000, and 1100 and their interaction. The magnetic hinge joint 20 lifts the posterior pharyngeal wall and maintains a patent airway. In essence, the magnetic attraction of the posterior region of the tongue to the palate holds the tongue in place so the tongue base can be repelled away from the pharyngeal walls.

From the foregoing embodiments, it can be appreciated that a magnetic force system 10 having regions of different magnetic interaction, attracting and repelling, can be variously configured. The size and configuration of the different regions can be altered to provide a larger repelling region than an attracting region, and vice versa. The size and configuration of the different structural locations of the implants can also be altered to provide greater stability in the repelling region.

In all the various embodiments, forces of magnetic attraction bring tissue together to form a magnetic hinge joint 20, providing an anchor to stabilize the regions where repelling forces work to separate tissue.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the technical features of the invention.

We claim:

1. An implant system comprising
a first magnetic component sized and configured to be implanted in the back of the tongue,
a second magnetic component sized and configured to be implanted across an airway from the first magnetic component in a posterior or posterior-lateral pharyngeal wall,
the airway having a midline, a first section and a second section,
each of the first and second magnetic components having a first portion disposed on a first side of the midline and a second portion disposed on a second side of the midline opposite the first portion,
the second portions of the first and second magnetic components magnetically repelling each other to open the first section of the airway on the second side of the midline, and
the first portions of the first and second magnetic components magnetically attracting each other to narrow or close the second section of the airway on the first side of the midline, thereby stabilizing the magnetic repulsion force between the second portions of the first and second magnetic components and the open first section of the airway.

2. An implant system comprising
a first magnetic component sized and configured to be implanted in the soft palate,
a second magnetic component sized and configured to be implanted across an airway from the first magnetic component in a posterior or posterior-lateral pharyngeal wall,
each of the first and second magnetic components having a first portion and a second portion,
the second portions of the first and second magnetic components magnetically repelling each other to lift the posterior or posterior-lateral pharyngeal wall away from the soft palate and open a section of the airway, and
the first portions of the first and second magnetic components magnetically attracting each other to narrow or close another section of the airway, thereby stabilizing the magnetic repulsion force between the second portions of the first and second magnetic components and the open section of the airway.

3. An implant system comprising
a first magnetic component sized and configured to be implanted in the posterior or posterior-lateral pharyngeal wall,
a second magnetic component sized and configured to be implanted adjacent to the first magnetic component in a posterior or posterior-lateral pharyngeal wall,
each of the first and second magnetic components having a first portion and a second portion,
the second portions of the first and second magnetic components magnetically repelling each other to move the posterior or posterior-lateral pharyngeal wall portions and open a section of the airway, and
the first portions of the first and second magnetic components magnetically attracting each other to narrow or close another section of the airway, thereby stabilizing the magnetic repulsion force between the second portions of the first and second magnetic components and the open section of the airway.

4. An implant system comprising
a first magnetic component sized and configured to be implanted in the back of the tongue,
a second magnetic component sized and configured to be implanted across an airway from the first magnetic component in a posterior or posterior-lateral pharyngeal wall,
a third magnetic component sized and configured to be implanted in the soft palate,
the first magnetic component having a first portion and a second portion,
the first portion of the first magnetic component and the second magnetic component magnetically repelling each other to open a first section of the airway, and
the second portion of the first magnetic component and the third magnetic component magnetically attracting each other to narrow or close a second section of the airway, thereby stabilizing the open first section of the airway.

5. An implant system according to claim 1, 2, 3, or 4 wherein the first portions of the first and second magnetic components have a surface area different than the second portions of the first and second magnetic components.

6. An implant system according to claim 1, 2, 3, or 4 wherein the second portions of the first and second magnetic components have a surface area larger than the first portions of the first and second magnetic components.

7. A method of treating an airway using an implant system as defined in claim 1, 2, 3, or 4.

8. An implant system comprising
a first magnetic component having a first portion and a second portion;
a second magnetic component having a first portion and a second portion;
wherein a magnetic attraction is developed between the first portion of the first magnetic component and the first portion of the second magnetic component, the first portion of the first magnetic component and the first portion of the second magnetic component being implanted opposite one another in a first tissue region,
wherein a magnetic repulsion is developed between the second portion of the first magnetic component and the second portion of the second magnetic component, the second portion of the first magnetic component and the second portion of the second magnetic component being implanted opposite one another in a second tissue region, and wherein the magnetic attraction between the first portion of the first magnetic component and first portion of the second magnetic component narrows the first tissue region and stabilizes the magnetic repulsion between the second portion of the first magnetic component and second portion of the second magnetic component which separates the second tissue region to create and maintain an open airway.

* * * * *